United States Patent
Zou et al.

(10) Patent No.: US 11,051,712 B2
(45) Date of Patent: Jul. 6, 2021

(54) SYSTEMS AND METHODS FOR DETERMINING THE LOCATION AND ORIENTATION OF IMPLANTED DEVICES

(71) Applicant: Verily Life Sciences LLC, Mountain View, CA (US)

(72) Inventors: You Zou, Sunnyvale, CA (US); Jiang Zhu, Cupertino, CA (US); Sean Korhummel, San Carlos, CA (US); Stephen O'Driscoll, San Francisco, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 958 days.

(21) Appl. No.: 15/019,641

(22) Filed: Feb. 9, 2016

(65) Prior Publication Data
US 2017/0224248 A1  Aug. 10, 2017

(51) Int. Cl.
*A61B 5/06* (2006.01)
*H04W 4/02* (2018.01)
(Continued)

(52) U.S. Cl.
CPC .............. *A61B 5/061* (2013.01); *A61B 5/062* (2013.01); *H04B 1/385* (2013.01); *H04W 4/025* (2013.01);
(Continued)

(58) Field of Classification Search
CPC ............ A61B 5/062; A61B 2560/0219; A61B 2562/046; A61B 5/0219;
(Continued)

(56) References Cited

U.S. PATENT DOCUMENTS 5,752,513 A * 5/1998 Acker ...................... A61B 5/06
                                                                128/899
5,967,980 A * 10/1999 Ferre ........................ A61B 5/06
                                                                600/424
(Continued)

FOREIGN PATENT DOCUMENTS

EP    1374792    1/2004
EP    1790279    5/2007
(Continued)

OTHER PUBLICATIONS

Shah et al. "Development of a tracking algorithm for an in-vivo RF capsule prototype" Dec. 19-21, 2006, 4th International Conference on Electrical and Computer Engineering ICECE, Bangladesh, pp. 173-176 (Year: 2006).*

(Continued)

*Primary Examiner* — Oommen Jacob
(74) *Attorney, Agent, or Firm* — Kilpatrick Townsend & Stockton LLP (57) ABSTRACT

The present disclosure relates to computerized systems and methods for determining the location and orientation of implanted devices. Consistent with some embodiments, power levels of near-field signals are backscattered from an implanted device. The backscattered near-field signals may be detected by an ex-vivo antenna array. The determined power levels may be used to identify candidate location and orientation combinations based on a data set. The data set may be generated by calibrating the antenna array to the implanted device. A candidate location and orientation combination among the identified candidate combinations may be selected as the location and orientation of the implanted device.

18 Claims, 7 Drawing Sheets

(51) Int. Cl.
*H04B 1/3827* (2015.01)
*H04W 4/80* (2018.01)

(52) U.S. Cl.
CPC ....... *H04W 4/80* (2018.02); *A61B 2560/0219* (2013.01); *A61B 2562/046* (2013.01)

(58) Field of Classification Search
CPC ............ A61B 5/061–063; H04W 4/80; H04W 4/025; H04B 1/385
USPC .................................................. 600/424, 407
See application file for complete search history.

(56) References Cited

U.S. PATENT DOCUMENTS

| | | | | |
|---|---|---|---|---|
| 6,206,835 | B1* | 3/2001 | Spillman, Jr. | A61B 5/0215 128/903 |
| 6,724,310 | B1* | 4/2004 | Gershenfeld | G08B 13/2414 340/572.1 |
| 7,590,441 | B2* | 9/2009 | Govari | A61B 5/06 600/407 |
| 7,603,160 | B2* | 10/2009 | Suzuki | A61B 1/041 128/899 |
| 7,725,151 | B2* | 5/2010 | van der Weide | A61B 5/0062 600/407 |
| 8,267,863 | B2* | 9/2012 | Najafi | A61N 1/365 600/302 |
| 8,357,111 | B2* | 1/2013 | Caillouette | A61B 5/061 602/26 |
| 8,634,928 | B1* | 1/2014 | O'Driscoll | A61N 1/37229 607/33 |
| 9,211,084 | B2* | 12/2015 | Uchiyama | A61B 1/00158 |
| 2002/0107445 | A1 | 8/2002 | Govari | |
| 2003/0018246 | A1* | 1/2003 | Govari | A61B 5/06 600/407 |
| 2003/0191430 | A1* | 10/2003 | D'Andrea | A61B 1/041 604/66 |
| 2004/0008123 | A1* | 1/2004 | Carrender | G06K 19/07749 340/8.1 |
| 2004/0153128 | A1* | 8/2004 | Suresh | G06F 19/3481 607/14 |
| 2004/0254457 | A1* | 12/2004 | van der Weide | A61B 5/0062 600/430 |
| 2005/0046608 | A1* | 3/2005 | Schantz | G01S 5/14 342/127 |
| 2005/0096589 | A1* | 5/2005 | Shachar | A61B 1/00158 604/95.01 |
| 2005/0143648 | A1* | 6/2005 | Minai | A61B 1/041 600/410 |
| 2005/0247319 | A1* | 11/2005 | Berger | A61B 90/90 128/898 |
| 2006/0058606 | A1* | 3/2006 | Davis | A61B 5/05 600/407 |
| 2006/0183993 | A1* | 8/2006 | Horn | A61B 1/00016 600/407 |
| 2006/0232408 | A1* | 10/2006 | Nycz | A61B 90/90 340/572.1 |
| 2007/0016006 | A1* | 1/2007 | Shachar | A61B 5/062 600/424 |
| 2007/0167743 | A1* | 7/2007 | Honda | A61B 1/041 600/424 |
| 2007/0182556 | A1* | 8/2007 | Rado | G01S 5/02 340/572.1 |
| 2007/0185398 | A1* | 8/2007 | Kimura | A61B 1/00158 600/424 |
| 2007/0210923 | A1* | 9/2007 | Butler | G06K 19/0723 340/572.8 |
| 2007/0238984 | A1* | 10/2007 | Maschke | A61B 5/0031 600/424 |
| 2007/0282196 | A1* | 12/2007 | Birk | A61B 5/06 600/424 |
| 2008/0027313 | A1* | 1/2008 | Shachar | A61B 1/00158 600/424 |
| 2008/0048907 | A1* | 2/2008 | Matsuura | G01S 3/808 342/147 |
| 2008/0154124 | A1* | 6/2008 | Iustin | A61B 5/06 600/424 |
| 2008/0165050 | A1* | 7/2008 | Schantz | G01S 5/14 342/165 |
| 2008/0306358 | A1* | 12/2008 | Minai | A61B 1/00036 600/302 |
| 2009/0062641 | A1* | 3/2009 | Barbu | A61B 34/20 600/424 |
| 2009/0303005 | A1* | 12/2009 | Tuttle | G06K 7/10009 340/10.1 |
| 2010/0085160 | A1* | 4/2010 | Fu | A61N 1/37223 340/10.1 |
| 2010/0125219 | A1* | 5/2010 | Harris | A61N 1/37229 600/544 |
| 2010/0156399 | A1* | 6/2010 | Chiba | A61B 1/00158 324/207.13 |
| 2011/0125007 | A1* | 5/2011 | Steinberg | A61B 1/00158 600/424 |
| 2011/0144479 | A1* | 6/2011 | Hastings | A61B 1/041 600/424 |
| 2011/0158488 | A1* | 6/2011 | Cohen | A61B 34/20 600/476 |
| 2011/0163882 | A1* | 7/2011 | August | G06Q 50/02 340/573.1 |
| 2011/0181273 | A1* | 7/2011 | Iida | A61B 1/00158 324/207.11 |
| 2011/0281535 | A1* | 11/2011 | Low | H02J 7/025 455/129 |
| 2011/0287784 | A1* | 11/2011 | Levin | H04W 64/00 455/456.2 |
| 2011/0304332 | A1* | 12/2011 | Mahfouz | A61F 2/3094 324/309 |
| 2011/0320170 | A1* | 12/2011 | Pathak | A61N 1/37223 702/183 |
| 2012/0004533 | A1* | 1/2012 | Peng | A61B 6/12 600/424 |
| 2012/0008714 | A1* | 1/2012 | Rizwan | A61B 5/0031 375/295 |
| 2012/0035495 | A1* | 2/2012 | Gutfinger | A61B 5/02 600/547 |
| 2012/0220855 | A1* | 8/2012 | Zhang | A61B 5/0037 600/410 |
| 2012/0224456 | A1* | 9/2012 | Visser | G01S 3/8006 367/127 |
| 2014/0167918 | A1* | 6/2014 | Stern | G06K 7/10009 340/10.1 |
| 2014/0257746 | A1* | 9/2014 | Dunbar | G01B 7/003 702/150 |
| 2017/0224248 | A1* | 8/2017 | Zou | A61B 5/061 |

FOREIGN PATENT DOCUMENTS

EP 2191768 6/2010
WO 2012104733 8/2012

OTHER PUBLICATIONS

Li et al. "Indoor Positioning Techniques Based on Wireless LAN," Mar. 2006, Proc. First IEEE Int'l Conf. Wireless Broadband and Ultra Wideband Comm. (Year: 2006).*

Pahlavan et al. "RF Localization for Wireless Video Capsule Endoscopy," 2012, Int. J. Wireless Inf. Networks, vol. 19, pp. 326-340 (Year: 2012).*

Basar et al. "Ingestible Wireless Capsule Technology: A Review of Development and Future Indication," 2012, International Journal of Antennas and Propagation, vol. 12, art. id No. 807165 (Year: 2012).*

Bras et al., A review of antennas for indoor positioning systems, 2012, International Journal of Antennas and Propagation, vol. 2012, art. id. No. 953269 (Year: 2012).*

Arab et al. "Investigation of Radar Localization System Accuracy for Human Gastro Intestine [GI] Tract", 2013, 7th International (56) References Cited

OTHER PUBLICATIONS

Symposium on Medical Information and Communication Technology, pp. 144-148 (Year: 2013).*
Zou et al. "Implant Position Estimation Via Wireless Power Link" IEEE Transactions on Circuits and Systems—II: Express Briefs, Feb. 2015, Published Online Dec. 2014, vol. 62, No. 2, pp. 139-143 (Year: 2014).*
Bao, "Chapter 2: Challenges in WCE Localization,"Apr. 2014, On Simultaneous Localization and Mapping inside the Human Body (Body-SLAM), Worcester Polytechnic Institute, Ph.D Thesis, pp. 9-27 (Year: 2014).*
Bitew et al. "Hybrid Indoor Human Localization System for Addressing the Issue of RSS Variation in Fingerprinting," 2015, International Journal of Distributed Sensor Networks, vol. 2015, art id. No. 831423 (Year: 2015).*
Besnoff ["Near Field Modulated Backscatter for In-Vivo Biotelemetry", 2012 IEEE International Conference on RFID (RFID)]. (Year: 2012).*
Zou ["Implant Position Estimation Via Wireless Power Link" IEEE Transactions on Circuits and Systems—II: Express Briefs, vol. 62, No. 2, Feb. 2015], (Year: 2015).*
Haselwander ["Measurement on an Active Phased Array Antenna on a Near-Field Range and an Anechoic Far-Field Chamber": 2001 31st European Microwave Conference, Sep. 2001] (Year: 2001).*
Chou ["Synthesis of Microstrip Antenna Arrays for Optimum Near-field Patterns via Steepest Decent Method", 2011 IEEE International Symposium on Antennas and Propagation (APSURSI)] (Year: 2011).*
Chou ["Design of Periodic Antenna Arrays With the Excitation Phases Synthesized for Optimum Near-Field Patterns via Steepest Descent Method" IEEE Transactions On Antennas and Propagation, vol. 59, No. 11, Nov. 2011] (Year: 2011 ).*
Zou ["Implant Positioning System Using Mutual Inductance" 34th Annual International Conference of the IEEE EMBS San Diego, California USA, Aug. 28-Sep. 1, 2012], (Year: 2012).*
Aubert "RFID technology for human implant devices" C. R. Physique 12 (2011) 675-683 (Year: 2011).*
Grant "Inductive Power Transfer" Proceedings of the IEEE | vol. 101, No. 6, Jun. 2013 (Year: 2013).*
Bashirullah "Wireless Implants" IEEE microwavemagazine Dec. 2010 Supplement (Year: 2010).*
Trung Duc Than et al., "A Review of Localization Systems for Robotic Endoscopic Capsules," IEEE Transactions on Biomedical Engineering (TBME), 2012 (13 pages).
John S. Ho et al., "Midfield Wireless Powering for Implantable Systems," Proceedings of the IEEE, 2013 (10 pages).
International Application No. PCT/US2017/015833 , "International Preliminary Report on Patentability", dated Aug. 23, 2018, 10 pages.
International Patent Application No. PCT/US2017/015833 , "International Search Report and Written Opinion", dated Apr. 25, 2017, 14 pages.

* cited by examiner

SYSTEMS AND METHODS FOR DETERMINING THE LOCATION AND ORIENTATION OF IMPLANTED DEVICES

BACKGROUND

The present disclosure generally relates to non-invasive techniques for locating an implanted device in an individual or other living being. More specifically, and without limitation, the present disclosure relates to computerized systems and methods for determining the location and orientation of implanted devices.

Implanted devices, such as devices implanted in the body of an individual or other living being, may be used for various functions. For example, an endoscopic capsule may be implanted to perform telemetry within the gastrointestinal tract of a subject. Endoscopic capsules may include various subsystems for collecting data about the subject such as, for example, a camera, an illumination system, a communications interface, and a local power supply for powering the subsystems. Other examples of implantable devices include a micro sensor or chip that can be implanted into upper layers of the skin to take various types of physiological measurements of a human wearer of the device.

In order to provide context to the collected data, systems and methods may be used to determine the location and orientation of an implanted device within the subject's body. The location and orientation information may provide important insight into where data was gathered or recorded. Some example techniques used to determine the location and orientation of an implanted device include far-field localization techniques based on phase-of-arrival or time-of-flight of signals transmitted by an in vivo capsule.

Methods and systems used to determine location and orientation of endoscopic capsules and other centimeter-sized implanted devices may not be suitable for use with sub-millimeter-sized implanted devices. Sub-millimeter devices may, for example, be implanted closer to the surface of the subject's body (e.g., subdermal implants) than centimeter-sized devices. Use of far-field localization techniques with these devices may therefore result in measurements that are too noisy. Moreover, time-based methods such as time-of-flight measurements may be unfeasible for these short-range measurements because they would require extremely strict time synchronization in order to obtain a sub-millimeter location and orientation resolution.

As another example, far-field localization techniques may not provide the granularity needed to accurately and precisely determine location and orientation of a sub-millimeter implanted device due to their small size relative to a centimeter-sized implanted device. For example, far-field localization techniques may only be able to determine an implanted device's location within several millimeters of error which may not suitable for devices less than a millimeter in size. Moreover, sub-millimeter implanted devices may lack on-board power supplies and communications interfaces due to size constraints and therefore signal transmissions from the device may not be available for performing phase-of-arrival or time-of-flight measurements.

SUMMARY

The present disclosure includes computerized systems and methods for determining the location and orientation of implanted devices. In illustrative embodiments, an ex-vivo antenna array is capable of transmitting wireless signals to an implanted device and measuring characteristics of near-field or intermediate-field backscattered from the implanted device. Illustrated embodiments consistent with the present disclosure also include computerized systems and methods for using the characteristics of the generated near-field to determine the location and orientation of the implanted device.

In accordance with one example embodiment, a system is provided for determining the location and orientation of an implanted device. The system includes a memory that stores a set of instructions and at least one processor in communication with the memory for executing the set of instructions. The at least one processor may be configured with the set of instructions to determine power levels of near-field signals backscattered from the implanted device, the near-field signals backscattered from the implanted device being detected by an ex-vivo antenna array. The at least one processor may also be configured to identify candidate location and orientation combinations corresponding to the determined power levels based on a data set. The data set may be generated from a calibration stage and stored in a database in various forms. The at least one processor may further be configured to select a candidate location and orientation combination among the identified candidate combinations as the location and orientation of the implanted device.

In accordance with another example embodiment, a computer-implemented method is provided for determining the location and orientation of an implanted device. The method includes determining power levels of near-field signals backscattered from the implanted device, the near-field signals backscattered from the implanted device being detected by an ex-vivo antenna array. Candidate location and orientation combinations corresponding to the determined power levels may be identified based on a data set. The data set may be generated from a calibration stage and stored in a database in various forms. A candidate location and orientation combination may be selected among the identified candidate combinations as the location and orientation of the implanted device.

In accordance with yet another example embodiment, a computer readable storage medium is provided including instructions executable by at least one processor to perform various operations. The operations include determining power levels of near-field signals backscattered from an implanted device. The near-field signals may be backscattered from the implanted device, the near-field signals backscattered from the implanted device being detected by an ex-vivo antenna array. The operations also include identifying candidate location and orientation combinations corresponding to the determined power levels based on a data set. The data set may be generated from a calibration stage and stored in a database in various forms. The operations further include selecting a candidate location and orientation combination among the identified candidate combinations as the location and orientation of the implanted device.

Before explaining certain embodiments of the present disclosure in detail, it is to be understood that the disclosure is not limited in its application to the details of construction and to the arrangements of the components set forth in the following description or illustrated in the drawings. The disclosure is capable of embodiments in addition to those described and of being practiced and carried out in various ways. Also, it is to be understood that the phraseology and terminology employed herein, as well as in the abstract, are for the purpose of description and should not be regarded as limiting.

As such, those skilled in the art will appreciate that the conception and features upon which this disclosure is based may readily be utilized as a basis for designing other structures, methods, and systems for carrying out the several purposes of the present disclosure. Furthermore, the claims should be regarded as including such equivalent constructions insofar as they do not depart from the spirit and scope of the present disclosure.

BRIEF DESCRIPTION OF DRAWINGS

The accompanying drawings, which are incorporated in and constitute part of this specification, and together with the description, illustrate and serve to explain the principles of various exemplary embodiments.

DETAILED DESCRIPTION OF EXAMPLE EMBODIMENTS

Embodiments of the present disclosure provide improved systems and methods for determining the location and orientation of implanted devices, such as sub-millimeter-sized implanted devices. The disclosed systems and methods are capable of determining location and orientation with sub-millimeter accuracy and without the need for power and data transmission subsystems on the implanted device. Accordingly, the disclosed location and orientation determination systems and methods allow for reductions in size and power consumption of implanted devices and are also capable of being used with passive implanted devices.

In accordance with some embodiments, the disclosed location and orientation determination systems and methods may include an ex-vivo antenna array capable of transmitting signals to an implanted device. Some of the transmitted signals in the near field of the antenna array transmission may be backscattered off the implanted device. The near-field may have various characteristics that can be used to determine location and/or orientation of the implanted device off which signals are backscattered.

According to some embodiments, the antenna elements in the antenna array may be calibrated before location/orientation determination. The calibration stage may produce a calibrated data set for use in conjunction with the characteristics of the backscattered near-field to identify candidate locations and/or orientations of the implanted device.

Reference will now be made in detail to the embodiments implemented according to the disclosure, the examples of which are illustrated in the accompanying drawings. Wherever possible, the same reference numbers will be used throughout the drawings to refer to the same or like parts.

Figure 1:
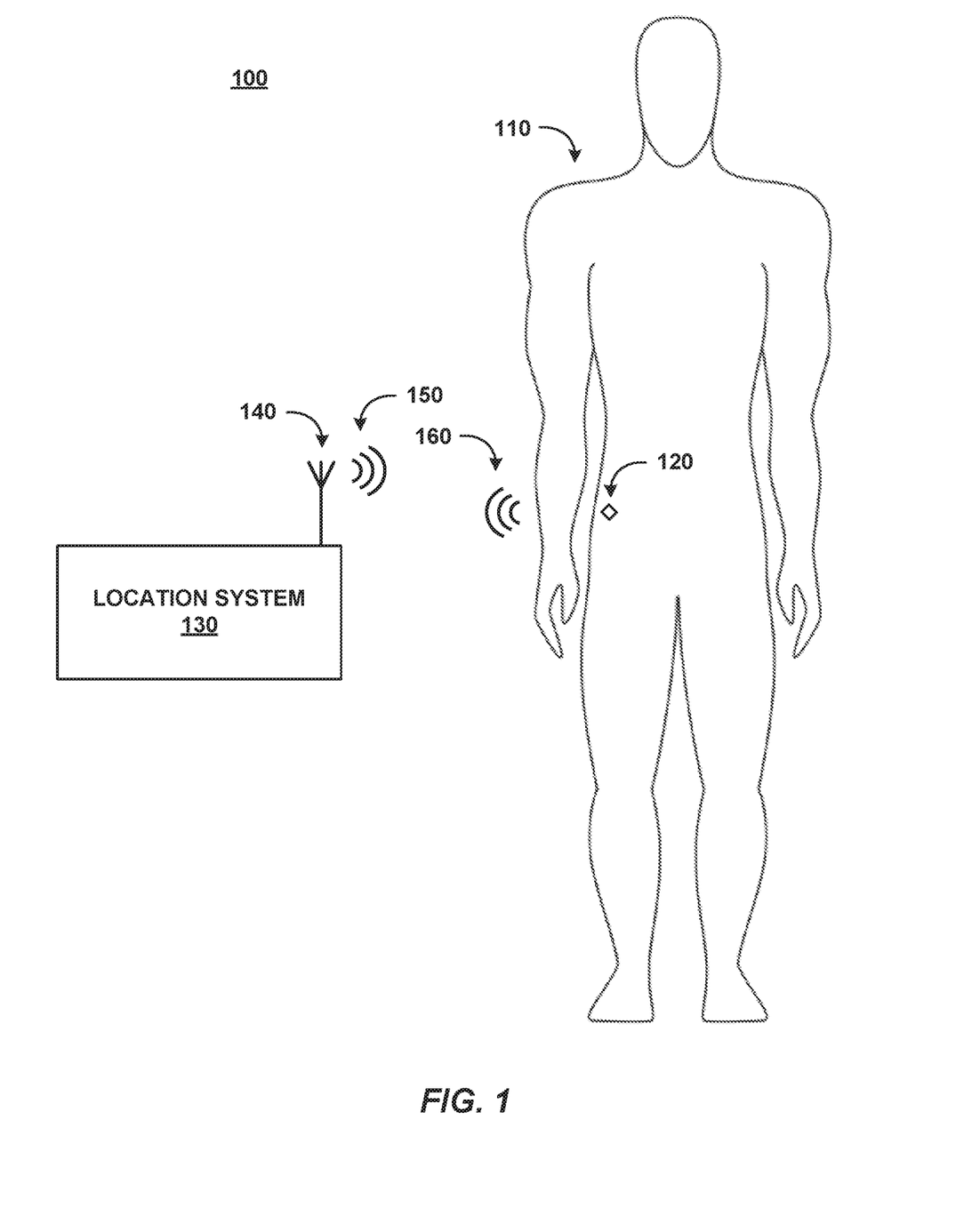
FIG. 1 is a diagram of an example system environment for implementing embodiments consistent with the present disclosure.

FIG. 1 depicts an example system environment 100 for implementing embodiments of the present disclosure. As shown in FIG. 1, system environment 100 includes a number of components. It will be appreciated from this disclosure that the number and arrangement of these components is exemplary only and provided for purposes of illustration. Other arrangements and numbers of components may be utilized without departing from the teachings and embodiments of the present disclosure.

As shown in the example embodiment of FIG. 1, system environment 100 may include an implanted device 120 and a location system 130. In some embodiments, implanted device 120 may be positioned in a subject 110. Subject 110 may be a human subject, an animal subject, or any other type of living subject. In some embodiments, implanted device 120 may be a sub-millimeter implanted device (i.e., a device having size dimensions less than one millimeter each). Implanted device 120 may be capable of being sub-dermally implanted a few millimeters beneath subject 110's skin. Other implant locations are contemplated and the preceding example is in no way intended to be limiting on the present disclosure.

Implanted device 120 may be a passive device that includes no power supply or other active subsystems. Alternatively, implanted device 120 may be an active device that includes a power supply and one or more subsystems for performing telemetry. Example subsystems include a camera, illumination subsystem, storage device, communications interface, etc. In embodiments where implanted device 120 is an active device, device 120 may transmit data to location system 130. The data may include pictures taken by a camera of implanted device 120, measurements such as voltage and current measurements taken by implanted device 120, and other sensor data or measurement information.

Location system 130 may be communicatively and/or physically coupled to one or more ex-vivo antenna arrays 140 that are capable of transmitting and receiving signals at various radio frequencies. Antenna array 140 may include one or more antenna elements (referred to herein as elements) that are arranged spatially from each other. The design aspects of antenna array 140 (e.g., element location, spacing, size and power, signal frequency, etc.) may be optimized for different implanted devices 120, different applications (e.g., different subjects 110), different implant locations, etc. For example, some antenna arrays 140 may be designed to be held close to the skin of subject 110 (e.g., on the skin of subject 110) and some antenna arrays 140 may be designed to be held further away. Accordingly, these differences in location may drive array element size, spacing, signal frequency, etc.

Transmitted signals 150 may include instructions such as, for example, instructions for implanted device 120 to perform telemetry by capturing data about the environment in which it is implanted. Transmitted signals 150 may alternatively, or in addition, include sufficient power for supplying implanted device 120 with power to run any subsystems included in implanted device 120. Received signals may include data such as, for example, pictures, streaming and/or recorded video, streaming and/or recorded audio, measurements, etc.

Location system 130 may transmit and receive data and power using various near-field transmission techniques. Such techniques may include non-radiative transmission techniques such as near-field coupling. Examples of near-field coupling include inductive coupling and capacitive coupling. In some embodiments, where location system 130 and implanted device 120 communicate via inductive coupling, antenna array 140 may generate a magnetic near-field to transmit data and/or power to implanted device 120. In some embodiments, where location system 130 and implanted device 120 communicate via capacitive coupling, antenna array 140 may generate an electric near-field to transmit data and/or power to implanted device 120.

In some embodiments, implanted device 120 may modulate the near-field generated by antenna array 140. For example, some of the generated near-field may backscatter (i.e., reflect) off of implanted device 120 and antenna array 140 may receive some of the backscattered near-field. The backscattered near-field 160 may be useful for determining the location and orientation of implanted device 120. For example, location system 130 may determine various characteristics of the backscattered near-field 160 received at antenna array 140 and compare these characteristics with characteristics of known location/orientation combinations of implanted device 120.

One characteristic that may be useful for location/orientation determination of implanted device 120 is the power level of backscattered near-field 160 received at antenna array 140. Location system 130 may include a spectrum analyzer that can analyze the received backscatter and determine the power level of the received near-field based on output from the spectrum analyzer. Near-field transmissions are particularly useful in this context, and provide significant advantages over far-field transmissions such as radar and sonar, because near-field transmission strength tends to decrease more rapidly with distance compared to far-field signals. For example, far-field transmissions attenuate near a rate proportional to the inverse of the range to the second power (i.e., $1/r^2$) whereas near-field transmissions attenuate near a rate proportional to the inverse of the range to the sixth power (i.e., $1/r^6$). The slower attenuation of far-field transmissions allows far-field signals to propagate over longer distances with relatively little power loss. However, the slow attenuation of far-field transmissions results in poor location/orientation granularity due to the greater distance traveled by a far-field transmission at each power level. Location and orientation determination using near-field transmissions may therefore provide more accurate and precise measurements of sub-millimeter devices than far-field techniques because near-field signals are more sensitive to small variations in distance.

In order to perform location and orientation determination of an implanted device 120, antenna array 140 can be calibrated for detection of different implanted devices. In some embodiments, the calibration may include performing live measurements of near-field backscattered off of implanted device 120 prior to implantation. A location, an orientation, or both a location and orientation may be assigned to each power level measurement collected by antenna array 140. In some embodiments, the calibration may include performing an electromagnetic simulation of the backscattered near-field reflected by implanted device 120 to obtain the backscattered power levels. Various simulation techniques may be used, for example, boundary element method, computational electrodynamics/electromagnetics, finite-difference time-domain, and particle-in-cell simulations.

Each measured/simulated power level and corresponding location and/or orientation may be recorded as a data set in a database in various forms. For example, a location may be defined by a two-dimensional distance from an array element ($d_x$, $d_z$) or a three-dimensional distance from an array element (e.g., $d_x$, $d_y$, $d_z$). An orientation may be defined in spherical coordinates (e.g., $\theta$, $\varphi$). The measured power levels may be defined in watts (W), decibel-milliwatts (dBm), decibel-watts (dBW), or any other unit of power. The database may be implemented as a look-up table, a spreadsheet, an eXtensible markup language ("XML") tree, or any other data structure or arrangement known in the art.

In some embodiments, each element in antenna array 140 may generate its own near-field that can be backscattered off implanted device 120. Each element may be separately calibrated to implanted device 120 and may have its own data set for the measured/simulated power levels and corresponding locations and/or orientations. The data sets for each element in antenna array 140 may be stored in the same database or separate databases.

In some embodiments, location system 130 may use the data sets generated from the calibration stage to perform location and/or orientation determination. Location system 130 may measure the power levels of near-field backscattered off of implanted device 120 and received at each element of antenna array 140. In one implementation, location system 130 may identify candidate locations and/or orientations in the calibrated data set for each element that corresponds to the measured power level at the respective element. Location system 130 may select a candidate location and/or orientation that are identified most frequently in the data sets as the location and/or orientation combination of implanted device 120. For example, if antenna array 140 includes three elements, and location system 130 identifies a candidate location of (0.2 mm dx, 0.4 mm $d_z$) that corresponds to measured power levels correspond in each data set for the three elements, then location system 130 may determine the location to be (0.2 mm dx, 0.4 mm $d_z$) relative to antenna array 140. In some embodiments, location system 130 may determine the location and/or orientation of implanted device 120 when each candidate location and/or orientation combination in the data sets overlap or match. In some embodiments, location system 130 may determine the location and/or orientation of implanted device 120 as the candidate location and/or orientation combination that occurs most frequently in the data sets. For example, if a candidate location (0.2 mm dx, 0.4 mm $d_z$) is identified in two out of three data sets for three elements in antenna array 140, and the third candidate location is identified as (0.4 mm dx, 0.4 mm $d_z$), then location system 130 may determine the location of implanted device 120 to be (0.2 mm dx, 0.4 mm $d_z$). The threshold amount of overlap may be selected depending on various factors such as, for example, the level of confidence required for the application, the measurement accuracy required, the required speed of the location/orientation determination, costs (e.g., system costs, testing costs), the level of granularity in the calibrated data sets, etc.

In another implementation for performing location and orientation determination, location system 130 may generate a model of the measured/simulated power levels collected during the calibration stage as a function of the spatial parameters of implanted device 120. In some embodiments, location system 130 may model the measured/simulated power levels collected during the calibration stage through curve fitting. For example, location system 130 may curve-fit the data points for each element in antenna array 140 as:

$$Pbs_{model,i} = f(d_x, d_y, d_z, \theta, \varphi)$$

where $Pbs_{model,i}$ is the modeled backscattered power level for the ith element in antenna array 140, $d_x$, $d_y$, $d_z$, are the offset of implanted device 120 from the ith element, and $\theta$ and φ are angular parameters that represent the orientation of device 120 in spherical coordinates.

Location system 130 may use the modeled power levels to iterate through solution sets using the measured power levels of near-field backscattered off of implanted device 120. Location system 130 may iterate through solution sets (i.e., spatial parameters of implanted device 120—$d_x$, $d_y$, $d_z$, θ, and φ) using the following expression:

$$\sum_{i=1}^{N} |Pbs_{model,i} - Pbs_{measured,i}|^2$$

where N is the number of elements in antenna array 140, $Pbs_{measured,i}$ is the measured backscattered power measured by the ith element in antenna array 140. Location system 130 may determine the location and/or orientation of implanted device 120 to be the solution set ($d_x$, $d_y$, $d_z$, θ, and φ) that minimizes the error produced by the expression (i.e., that produces the lowest error). As will be appreciated from this disclosure, the preceding expression is exemplary only and other expressions or optimization algorithms may be used. Alternative optimization algorithms include Newton's method, a particle swarm optimization algorithm, the Bees Algorithm, a particle filter, etc.

Figure 2:
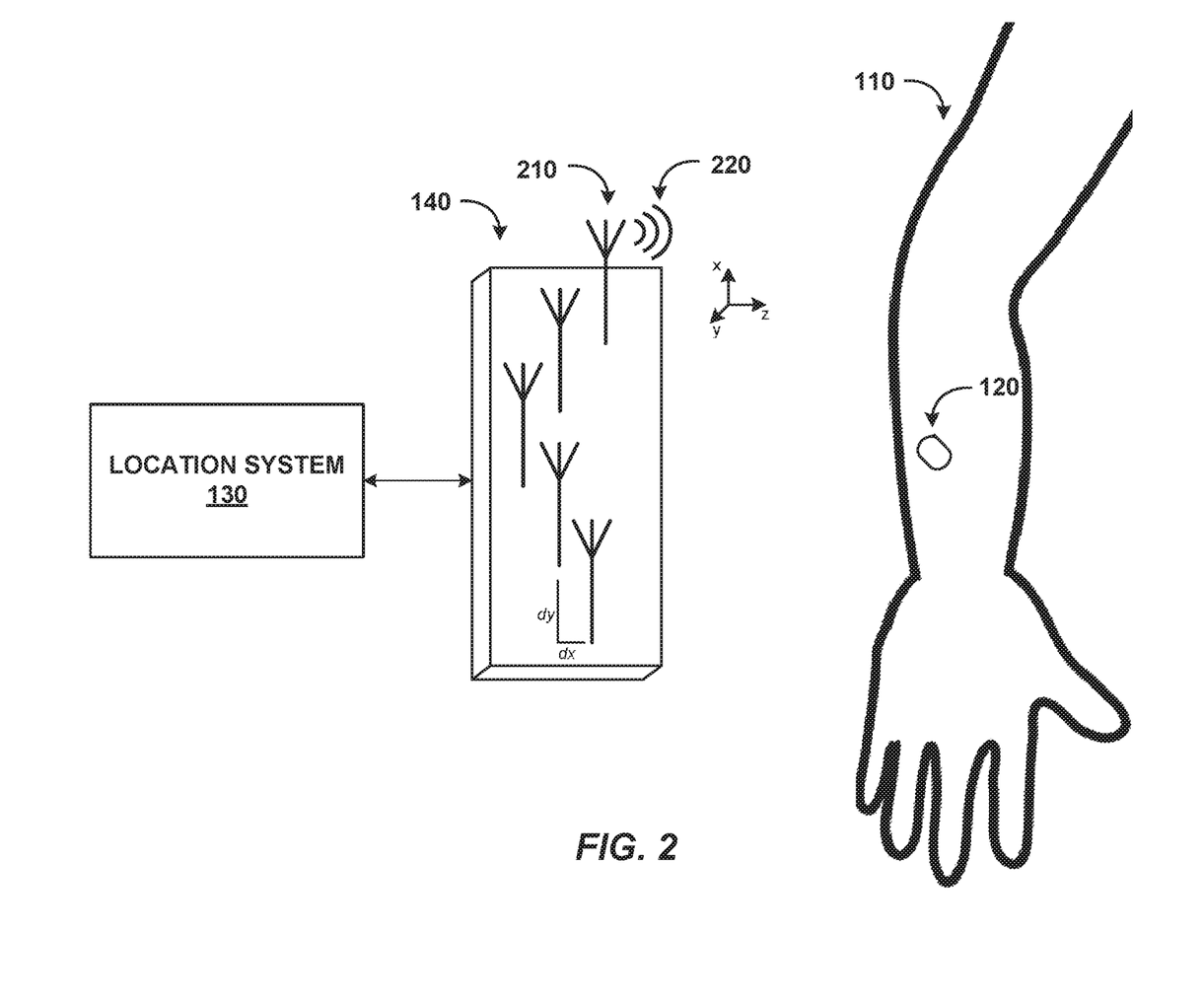
FIG. 2 depicts another view of the example system environment shown in FIG. 1.

FIG. 2 depicts another view of example system environment 100 shown in FIG. 1. As shown in the example embodiment of FIG. 2, antenna array 140 may include a plurality of elements 210 that may transmit signals 220. Each element 210 may be spaced from each other a distance $d_x$, $d_y$. The arrangement and spacing of elements 210 as shown in FIG. 2 is exemplary only and other spacing, number, and arrangements are contemplated. For example, elements 210 may be spaced in an additional z direction, may be rotated at various orientations about one or more axes, may be different shapes/sizes, etc.

Each element 210 may couple with implanted device 120 (implanted in an arm of subject 110 as illustrated in the example in FIG. 2) by generating a near-field via transmitted signals 220. Implanted device 120 may backscatter some of the generated near-field to elements 210. Each element 210 may measure the power levels of the backscattered near-field and transmit the measured power levels to location system 130 for location and/or orientation determination of implanted device 120.

Figure 3:
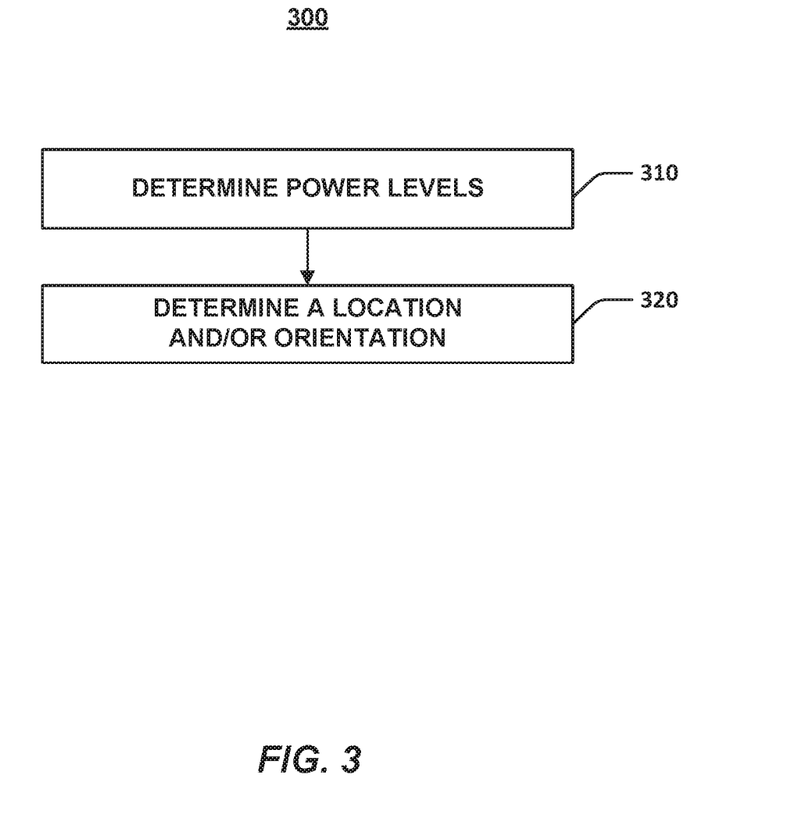
FIG. 3 is a flow diagram depicting an example process for location and/or orientation determination, in accordance with an embodiment of the present disclosure.

FIG. 3 depicts a flowchart of an example method 300, consistent with some embodiments and aspects of the present disclosure. Method 300 may be implemented, for example, for determining location and/or orientation of an implanted device. The number and sequence of operations in FIG. 3 are provided for purposes of illustration and may be modified, enhance, substituted, or otherwise changed, in view of the present disclosure. In some embodiments, portions of method 300 may be implemented as one or more computer programs executed by one or more processors. Moreover, in some embodiments, method 300 may be implemented by a location system (e.g., location system 130 having one or more processors executing one or more computer programs stored on a non-transitory computer readable medium) and an antenna array (e.g., antenna array 140 having one or more elements 210).

In some embodiments, example method 300 may include determining power levels at 310. For example, the location system may generate a near-field by transmitting signals via the antenna array. The generated near-field may couple with an implanted device (e.g., implanted device 120 of FIG. 1). Location system 130 may transmit data and/or power to the implanted device via the coupled near-field. In some embodiments, the implanted device may backscatter some of the near-field to the antenna array. The location system may receive the backscattered near-field via the antenna array and determine the power levels therefrom. For example, the location system may include a spectrum analyzer that analyzes the received backscatter and location system determines the power level of the received near-field based on output from the spectrum analyzer.

In some embodiments, each element in the array may generate a near-field and receive signals backscattered from the implanted device. The location system may determine the power levels of backscatter received at each element.

In some embodiments, example method 300 may include determining a location and/or orientation of the implanted device at 320. The antenna array may be calibrated to the implanted device. The calibration stage may produce a calibrated data set that can be used to determine the location and/or orientation of the implanted device. The calibrated data set may include combinations of measured or simulated power levels from the calibration stage that corresponds to candidate locations and/or orientations of the implanted device. The location system may use the identified candidate location and/or orientations corresponding to the power levels determined at 310. The location system may select a candidate location and/or orientation among the identified candidate locations and/or orientations as the location and/or orientation of the implanted device using various techniques. For example, the location system may select a candidate location and/or orientation among the identified locations and/or orientations as the location and/or orientation of the implanted device using method 400 described below in FIG. 4, method 600 described below in FIG. 6, and/or other techniques, as appreciated from this disclosure.

In some embodiments, each element in the antenna array may calibrated to the implanted device and may have its own calibrated data set. The location system may determine the location and/or orientation using the calibrated data sets of each calibrated element. For example, the location system may identify candidate location and/or orientations in each data set for each element corresponding to the power levels of backscatter received the respective element. The location system may select a candidate location and/or orientation among the candidate locations and/or orientations identified for each element as the location and/or orientation of the implanted device using the example embodiments disclosed herein and/or other techniques.

Figure 4:
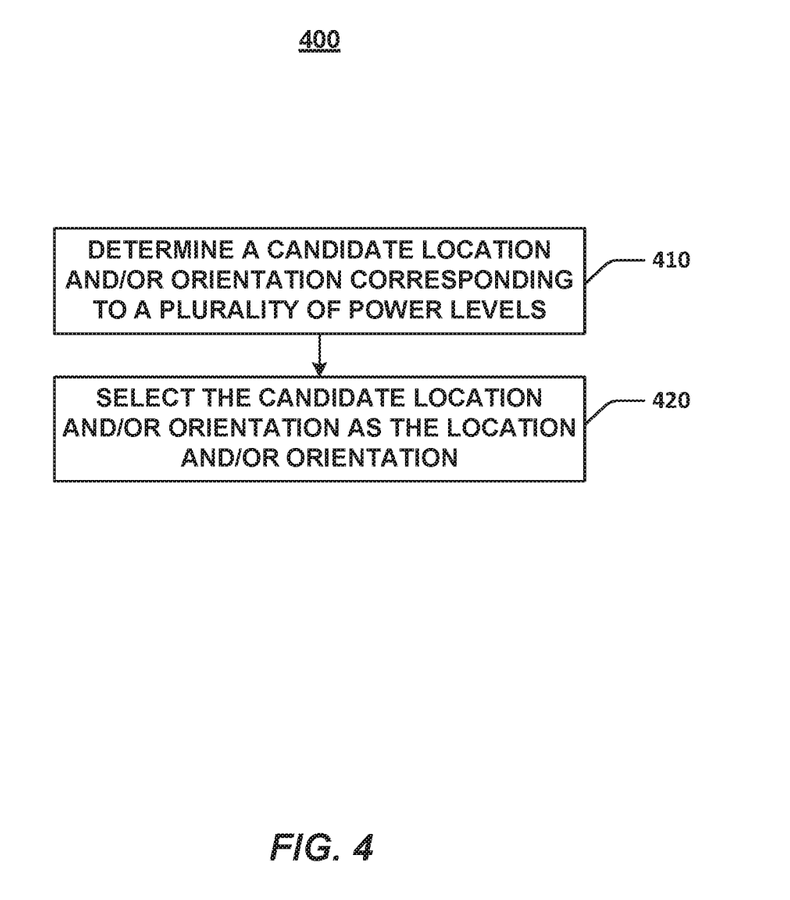
FIG. 4 is a flow diagram depicting another example process for location and/or orientation determination, in accordance with an embodiment of the present disclosure.

FIG. 4 depicts a flowchart of an example method 400, consistent with some embodiments and aspects of the present disclosure. Method 400 may be implemented, for example, for determining a location and/or orientation of an implanted device. The number and sequence of operations in FIG. 4 are provided for purposes of illustration and may be modified, enhance, substituted, or otherwise changed, in view of the present disclosure. In some embodiments, portions of method 400 may be implemented as one or more computer programs executed by one or more processors. Moreover, in some embodiments, method 400 may be implemented by a location system and an antenna array. Method 400 may be performed as part of 320 of method 300. Alternatively, method 400 may be performed independently of method 300.

In some embodiments, example method 400 may include determining a location and/or orientation that corresponds to a plurality of determined power levels at 410. For example, the power levels may be determined at 310 of method 300. The location system may compare the determined power levels to the power levels stored in the data set to determine if there are any stored power levels that match the determined power levels. In some embodiments, where the antenna array includes a plurality of elements that determine power levels at 310, location system may compare the power levels determined at each element to the power levels stored in their respective data set to determine matches. When a matching power level is found in a data set, the location system may identify the candidate location and/or orientation corresponding to the matched power level.

The location system may determine a location and/or orientation that corresponds to a plurality of the determined power levels at 310. For example, the location system may compare the candidate locations and/or orientations that correspond to matched power levels in each data set to each other to determine if any duplicate candidate locations and/or orientations have been identified. For example, if the antenna array includes three elements, and location system determines that the determined power levels at each element corresponds to a location of (0.6 mm dy, 0.2 mm dx), the location system may determine the location (0.6 mm dy, 0.2 mm dx) to be a location that corresponds to a plurality of determined power levels.

In some embodiments, example method 400 may include selecting the location and/or orientation determined as 410 as the location and/or orientation of the implanted device at 420. In some embodiments, the location system may select the location and/or orientation when the location and/or orientation corresponds to the power levels determined at all of the elements in the array. In some embodiments, the location system may select the location and/or orientation when the location and/or orientation corresponds to the power levels determined at less than all of the elements in the array. For example, the location system may select the location and/or orientation when the location and/or orientation corresponds to the power levels determined at a majority of the elements in the array or another threshold number of elements in the array.

Figure 5:
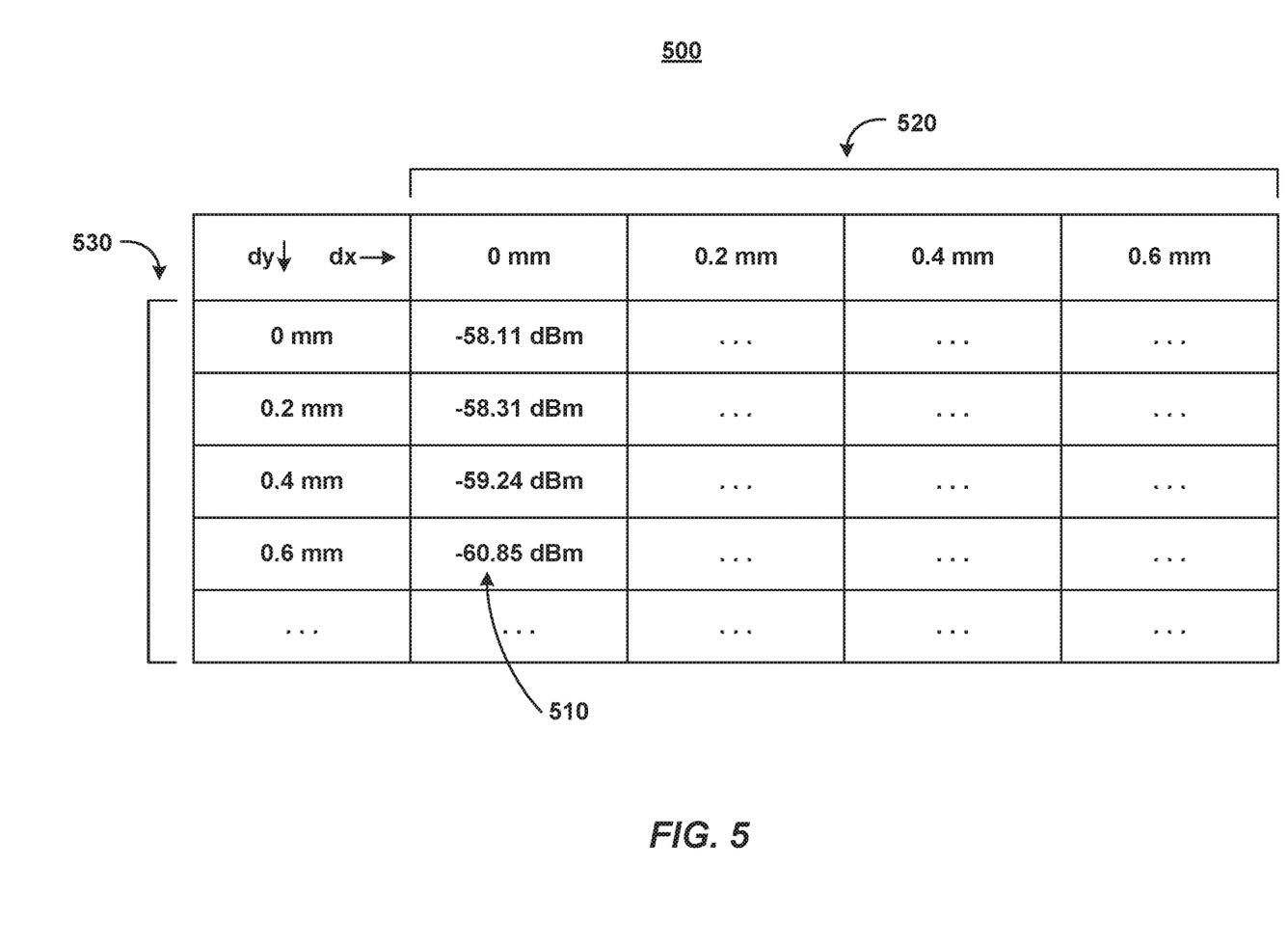
FIG. 5 illustrates an example implementation of a data set for location and/or orientation determination, in accordance with an embodiment of the present disclosure.

FIG. 5 illustrates an example implementation of a data set 500 that corresponds to an element in an antenna array. In some embodiments, data set 500 may be used for location and/or orientation determination of implanted devices as part of method 400 of FIG. 4. As shown in FIG. 5, data set 500 may be implemented as a look-up table that stores various power levels 510. Each power level 510 may be generated in a calibration stage by taking power level measurements or by simulation as described above in reference to FIG. 1. Each power level 510 may correspond to a displacement of an implanted device from each element in the antenna array. As illustrated in the example of FIG. 5, the displacements may include pairs of x coordinate displacements 520 and y displacements 530 specifying the amount of distance from the element along the x axis and y axis, respectively.

Figure 6:
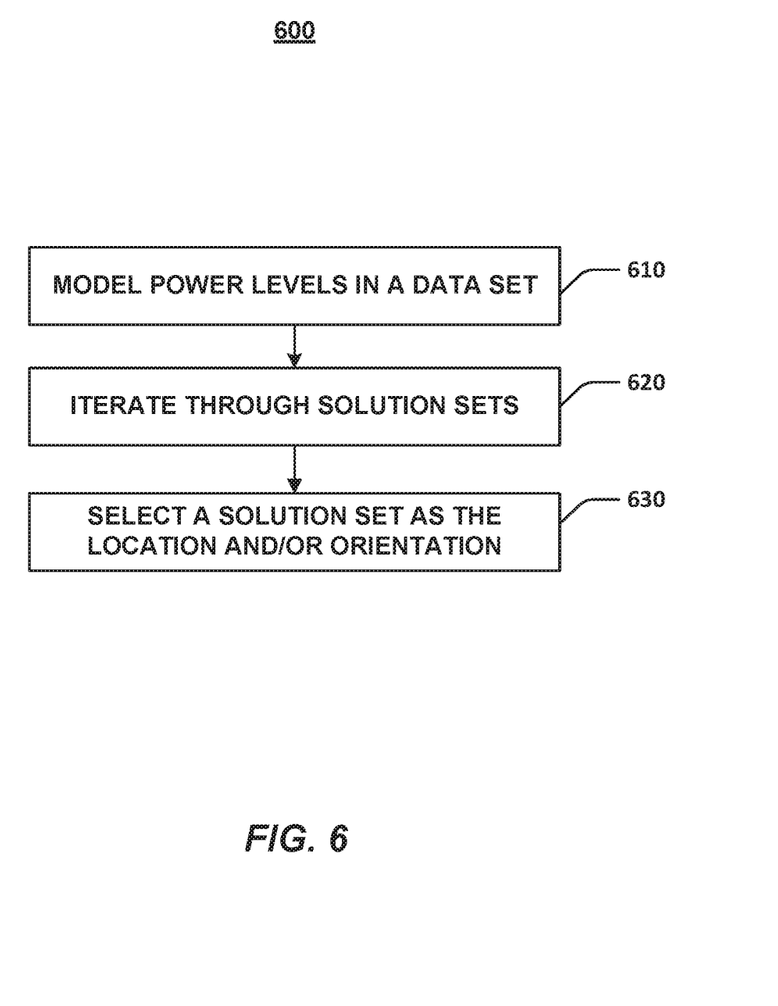
FIG. 6 is a flow diagram depicting another example process for location and/or orientation determination, in accordance with an embodiment of the present disclosure.

FIG. 6 depicts a flowchart of an example method 600, consistent with some embodiments and aspects of the present disclosure. Method 600 may be implemented, for example, for determining a location and/or orientation of an implanted device. The number and sequence of operations in FIG. 6 are provided for purposes of illustration and may be modified, enhance, substituted, or otherwise changed, in view of the present disclosure. In some embodiments, portions of method 600 may be implemented as one or more computer programs executed by one or more processors. Moreover, in some embodiments, method 600 may be implemented by a location system and an antenna array. Method 600 may be performed as part of 320 of method 300. Alternatively, method 600 may be performed independently of method 300.

In some embodiments, example method 600 may include modeling the power levels included in the data set at 610. For example, the location system may model the power levels included in the data set through curve fitting or other techniques described above in reference to FIG. 1.

In some embodiments, example method 600 may include iterating through identified candidate locations and/or orientations using the generated model at 620. For example, the location system may use the identified candidate locations and/or orientations as solution sets for an optimization algorithm. The optimization algorithm may be one of the optimization algorithms described above in reference to FIG. 1 and may use the model generated at 610 and the solution sets to determine an amount of error. For example, the location system may process each solution set through the optimization algorithm to determine the amount of error produced by the solution set in the optimization algorithm.

In some embodiments, example method 600 may include selecting a location and/or orientation based on the iterative process at 630. For example, the location system may select the location and/or orientation for the implanted device as the solution set that produces the lowest error from the optimization algorithm.

Embodiments described above include computer-implemented methods, tangible non-transitory computer-readable mediums, and systems. The computer-implemented methods may be executed, for example, by at least one processor that receives instructions from a non-transitory computer-readable storage medium. Similarly, systems consistent with the present disclosure may include at least one processor and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, nonvolatile memory, hard drives, compact disk read-only memories ("CD ROMs"), digital versatile disks ("DVDs"), flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

Figure 7:
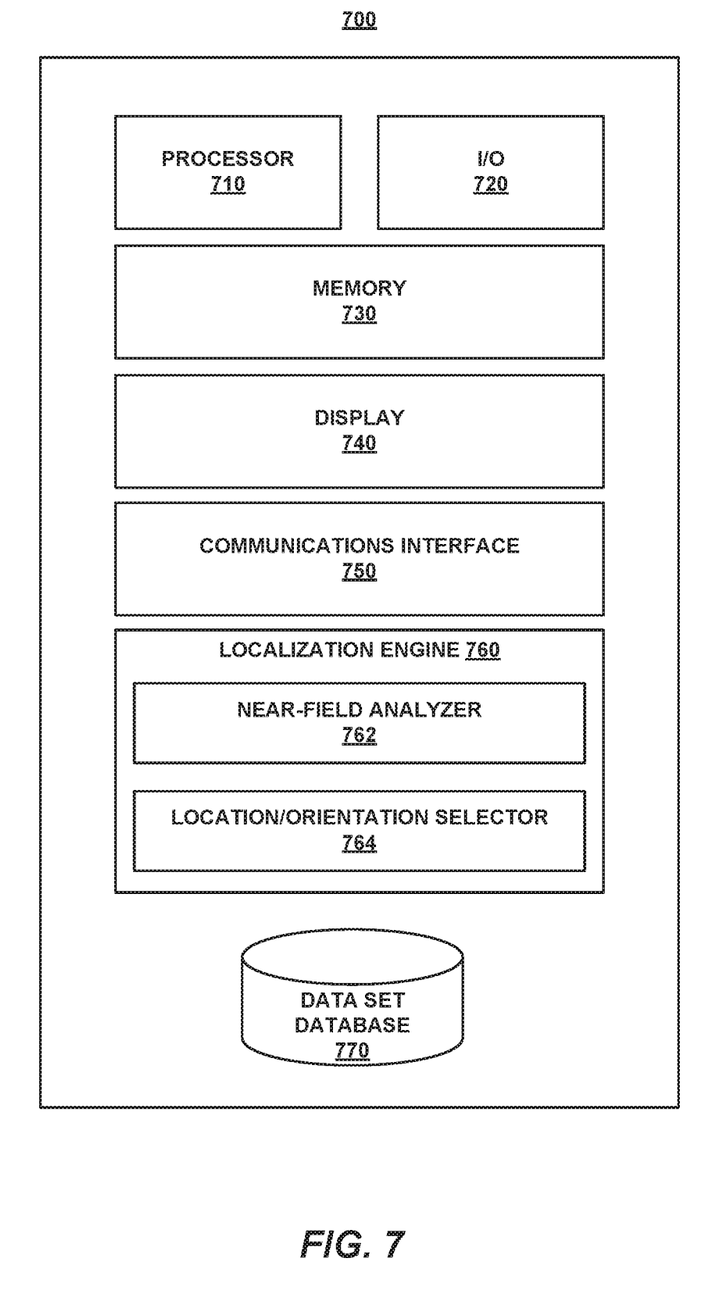
FIG. 7 illustrates an example system for implementing some embodiments and aspects of the present disclosure.

FIG. 7 illustrates an example system 700 for implementing embodiments and aspects of the present disclosure described above. By way of example, system 700 may be used to implement location system 130 of FIG. 1 and may be communicatively and/or physically coupled to an antenna array (e.g., antenna array 140 of FIG. 1). The arrangement and number of components in system 700 is provided for purposes of illustration. Additional arrangements, number of components, and other modifications may be made, consistent with the present disclosure.

As shown in FIG. 7, system 700 may include one or more processors 710 for executing instructions. Processors suitable for the execution of instructions include, by way of example, both general and special purpose microprocessors, and any one or more processors of any kind of digital computer. System 700 may also include one or more input/output (I/O) devices 720. By way of example, I/O devices 720 may include physical keyboards, virtual touch-screen keyboards, mice, joysticks, styluses, etc. Moreover, I/O devices 720 may include loudspeakers, handset speakers, microphones, cameras, or sensors such as accelerometers, temperature sensors, or photo/light sensors.

As further illustrated in FIG. 7, system 700 may include one or more storage devices configured to store data and/or software instructions used by the one or more processors 710 to perform operations consistent with disclosed aspects and embodiments herein. For example, system 700 may include a memory 730 configured to store one or more software programs that performs functions or operations when executed by the one or more processors 710. By way of example, memory 730 may include NOR or NAND flash memory devices, Read Only Memory (ROM) devices, Random Access Memory (RAM) devices, etc. Memory 730 may also include storage mediums such as, for example, hard drives, solid state drives, tape drives, redundant array of inexpensive disks ("RAID") arrays, etc. Although FIG. 7 shows only one memory 730, system 700 may include any number of memories 730. Further, although FIG. 7 shows memory 730 as part of system 700, memory 730 may be located remotely and system 700 may be able to access memory 730 via a network.

System 700 may also include one or more displays 740 for displaying data and information. For example display 740 may be configured to display data received from an implanted device (e.g., implanted device 120 of FIG. 1) and determined locations and/or orientations of an implanted device. Display 740 may be implemented using devices or technology, such as a cathode ray tube (CRT) display, a liquid crystal display (LCD), a plasma display, a light emitting diode (LED) display, a touch screen type display such as capacitive or resistive touchscreens, and/or any other type of display known in the art.

System 700 may also include one or more communications interfaces 750. Communications interface 750 may allow software and data to be transferred between system 700, a network, a database, other systems, and/or other components. Examples of communications interface 750 may include a modem, a wired or wireless communications interface (e.g., an Ethernet, Wi-Fi, Bluetooth, Near Field Communication, worldwide interoperability for Microwave Access ("WiMAX"), wide area network ("WAN"), local area network ("LAN"), etc.), a communications port (e.g., universal serial bus ("USB"), IEEE 1394, DisplayPort, digital visual interface ("DVI"), high-definition multimedia interface ("HDMI"), video graphics array ("VGA"), Serial port, etc.), a personal computer memory card international association ("PCMCIA") slot and card, etc. Communications interface 750 may transfer software and data in the form of signals, which may be electronic, electromagnetic, optical, or other signals capable of being received by communications interface 750. These signals may be provided to communications interface 750 via a communications path (not shown), which may be implemented using wireless, wire, cable, fiber optics, radio frequency ("RF") link, and/or other communications channels.

System 700 may include a localization engine 760. By way of example, localization engine 760 may be configured to determine locations and/or orientations of implanted devices in accordance with the preceding disclosure. In some embodiments, localization engine 760 may include a near-field analyzer 762 and a location/orientation selector 764. Components 762 and 764 may be implemented as hardware modules configured to execute the functions described herein. Alternatively, processor 710 may be configured to execute the functions of components 762 and 764. For example, processor 710 may communicate with memory 730 that includes components 762 and 764 in the form of computer-executable instructions, such that processor 710 may then execute these instructions. As another example, the functions of components 762 and 764 may be included in processor 710 itself, such that processor 710 is configured to implement these functions.

Near-field analyzer 762 may analyze characteristics of near-field transmitted by an antenna array and backscattered from an implanted device. For example, near-field analyzer 762 may determine power levels of near-field backscatter received at each element of the antenna array.

Location/orientation selector 764 may determine locations and/or orientations of implanted devices. For example, location/orientation selector 764 may determine locations and/or orientations of implanted devices using the features and embodiments described above with reference to FIGS. 1-6.

Data set database 770 may be used to store data sets generated from the calibration of each element in the antenna array. Data set database 770 may include one or more logically and/or physically separate databases configured to store the data sets. The data sets stored in data set database 770 may be received from a server, a client, and/or may be provided as input using conventional methods (e.g., data entry, data transfer, data uploading, etc.). The data sets stored in the data set database 770 may take or represent various forms including, but not limited to, documents, look-up tables, spreadsheets, XML trees, or any combination thereof.

In some embodiments, data set database 770 may be implemented using any suitable form of a computer-readable storage medium. In some embodiments, data set database 770 may be maintained in a network attached storage device, in a storage area network, or combinations thereof, etc. Furthermore, data set database 770 may be maintained and queried using numerous types of database software and programming languages, for example, SQL, MySQL, IBM DB2®, Microsoft Access®, PERL, C/C++, Java®, etc. Although FIG. 7 shows data set database 770 associated with location system 130, data set database 770 may be a standalone database that is accessible via a network.

The disclosed embodiments are not limited to separate programs or computers configured to perform dedicated tasks. For example, location system 130 may include memory 730 that stores a single program or multiple programs. Additionally, location system 130 may execute one or more programs located remotely from location system 130. In some example embodiments, location system 130 may be capable of accessing separate web server(s) or computing devices that generate, maintain, and provide web sites and/or event creation and notification services.

In the preceding specification, various exemplary embodiments and features have been described with reference to the accompanying drawings. It will, however, be evident that various modifications and changes may be made thereto, and additional embodiments and features may be implemented, without departing from the broader scope of the invention as set forth in the claims that follow. The specification and drawings are accordingly to be regarded in an illustrative rather than restrictive sense.

For example, while the embodiments described above use near-field backscatter for location/orientation determination, the described embodiments may also use intermediate-field backscatter to achieve similar results. Additionally, advantageous results still could be achieved if the steps or operations of the disclosed techniques were performed in a different order and/or if components in the disclosed systems were combined in a different manner and/or replaced or supplemented by other components. Moreover, while embodiments of the present disclosure have been described with reference to the processing of point-of-interest data, embodiments of the present disclosure may be applied to process and ingest other types of data. Other implementations are also within the scope of the following exemplary claims.

Therefore, it is intended that the disclosed embodiments and examples be considered as exemplary only, with a true scope of the present disclosure being indicated by the following claims and their equivalents.

What is claimed is:

1. A system for determining a location or orientation of an implanted device, the system comprising:
    a memory device that stores a set of processor-executable instructions; and
    at least one processor configured to execute the instructions to:
        cause an ex-vivo antenna array to transmit first near-field signals, the ex-vivo antenna array comprising a plurality of antennas;
        determine power levels of second near-field signals backscattered from an antenna of the implanted device based on the first near-field signals, the second near-field signals backscattered by the antenna of the implanted device being detected by the ex-vivo antenna array;
        identify candidate locations or orientations corresponding to the implanted device based on the determined power levels based on a data set; and
        select a candidate location or orientation among the identified candidate locations or orientations as the location or orientation of the implanted device.

2. The system according to claim 1, wherein the data set is included in at least one of a look-up table, an XML tree, and a spreadsheet.

3. The system according to claim 1, wherein the at least one processor is configured to execute the instructions to select the candidate location or orientation, including instructions to:
    determine, among the identified candidate locations or orientations, a location or orientation that corresponds to a plurality of the determined power levels; and
    select the determined location or orientation as the location or orientation of the implanted device.

4. The system according to claim 1, wherein the at least one processor is further configured to execute the instructions to:
    determine power levels of the second near-field signals backscattered from the implanted device and detected at each antenna coil in the ex-vivo antenna array; and
    identify candidate locations or orientations included in a plurality of data sets that correspond to the determined power levels, each of the plurality of data sets associated with specific ones of the antennas in the ex-vivo antenna array.

5. The system according to claim 4, wherein the at least one processor is further configured to execute the instructions to:
    determine, among the identified candidate locations or orientations, a location or orientation identified in each of the plurality of data sets; and
    select the determined location or orientation as the location or orientation of the implanted device.

6. The system according to claim 1, wherein the first near-field signals transmitted to the implanted device by the ex-vivo antenna array are configured to power the implanted device wirelessly.

7. The system according to claim 1, wherein the at least one processor is configured to execute the instructions to select the candidate location or orientation, including instructions to:
    generate a model of power levels included in the data set;
    iterate through the identified candidate locations or orientations using the model based on an optimization algorithm; and
    select a candidate location or orientation among the identified candidate locations or orientations as the location or orientation of the implanted device based on the iteration through the identified candidate locations or orientations.

8. The system according to claim 7, wherein the at least one processor is configured to execute the instructions to select the candidate location or orientation, including instructions to:
    select a candidate location or orientation among the identified candidate locations or orientations that produces the lowest error of the optimization algorithm as the location or orientation of the implanted device.

9. A method for determining a location or orientation of an implanted device, the method performed by at least one processor and comprising:
    causing an ex-vivo antenna array to transmit first near-field signals, the ex-vivo antenna array comprising a plurality of antennas;
    determining power levels of second near-field signals backscattered by an antenna of the implanted device based on the first near-field signals, the second near-field signals being detected by the ex-vivo antenna array;
    identifying candidate locations or orientations corresponding to the implanted device based on the determined power levels based on a data set; and
    selecting a candidate location or orientation among the identified candidate locations or orientations as the location or orientation of the implanted device.

10. The method according to claim 9, wherein the data set is included in at least one of a look-up table, an XML tree, and a spreadsheet.

11. The method according to claim 9, wherein selecting a candidate location or orientation among the identified candidate locations or orientations includes:
    determining, among the identified candidate locations or orientations, a location or orientation that corresponds to a plurality of the determined power levels; and
    selecting the determined location or orientation as the location or orientation of the implanted device.

12. The method according to claim 9, wherein:
    determining power levels of the second near-field signals backscattered from the implanted device includes determining power levels of the second near-field signals backscattered from the implanted device detected at each element in the ex-vivo antenna array; and identifying candidate locations or orientations includes identifying candidate locations or orientations included in a plurality of data sets that correspond to the determined power levels, each of the plurality of data sets associated with specific ones of the elements in the ex-vivo antenna array.

13. The method according to claim 12, further comprising:

determining, among the identified candidate locations or orientations, a location or orientation identified in each of the plurality of data sets; and selecting the determined location or orientation as the location or orientation of the implanted device.

14. The method according to claim 9, wherein the first near-field signals transmitted to the implanted device by the ex-vivo antenna array power the implanted device wirelessly.

15. The method according to claim 9, wherein selecting the candidate locations or orientations among the identified candidate locations or orientations includes:

generating a model of power levels included in the data set;

iterating through the identified candidate locations or orientations using the model based on an optimization algorithm; and selecting a candidate location or orientation among the identified candidate locations or orientations as the location or orientation of the implanted device based on the iteration through the identified candidate locations or orientations.

16. The method according to claim 15, wherein selecting the candidate location or orientation among the identified candidate locations or orientations includes:

selecting a candidate location or orientation among the identified candidate locations or orientations that produces the lowest error of the optimization algorithm as the location or orientation of the implanted device.

17. A non-transitory computer-readable medium including instructions that, when executed by at least one processor, cause the at least one processor to:

cause an ex-vivo antenna array to transmit first near-field signals, the ex-vivo antenna array comprising a plurality of antennas;

determine power levels of second near-field signals backscattered by an antenna of an implanted device based on the first near-field signals, the second near-field signals backscattered from the implanted device being detected by the ex-vivo antenna array;

identify candidate locations or orientations corresponding to the implanted device based on the determined power levels based on a data set; and select a candidate location or orientation among the identified candidate locations or orientations as the location or orientation of the implanted device.

18. The non-transitory computer-readable medium according to claim 17, wherein the non-transitory computer-readable medium further comprises instructions that, when executed by the at least one processor, cause the at least one processor to:

determine, among the identified candidate locations or orientations, a location or orientation that corresponds to a plurality of the determined power levels; and select the determined candidate location or orientation as the location or orientation of the implanted device.

* * * * *